US012766171B2

(12) United States Patent
Suñé Negre et al.

(10) Patent No.: US 12,766,171 B2
(45) Date of Patent: Oct. 20, 2026

(54) LONG-TERM STABLE LIVE FECAL MICROBIOTA COMPOSITION

(71) Applicants: FUNDACIÓ DE RECERCA CLÍNIC BARCELONA-INSTITUT D'INVESTIGACIONS BIOMÈDIQUES AUGUST PI I SUNYER, Barcelona (ES); HOSPITAL CLÍNIC DE BARCELONA, Barcelona (ES); UNIVERSITAT DE BARCELONA, Barcelona (ES)

(72) Inventors: Josep M. Suñé Negre, Barcelona (ES); Alex Soriano Viladomiu, Barcelona (ES); Andrea Aira Gomez, Barcelona (ES); Csaba Feher, Barcelona (ES)

(73) Assignees: FUNDACIÓ DE RECERCA CLÍNIC BARCELONA-INSTITUT D'INVESTIGACIONS BIOMÈDIQUES AUGUST PI I SUNYER, Barcelona (ES); HOSPITAL CLÍNIC DE BARCELONA, Barcelona (ES); UNIVERSITAT DE BARCELONA, Barcelona (ES)

( * ) Notice: Subject to any disclaimer, the term of this patent is extended or adjusted under 35 U.S.C. 154(b) by 875 days.

(21) Appl. No.: 17/602,134

(22) PCT Filed: Apr. 14, 2020

(86) PCT No.: PCT/EP2020/060370
§ 371 (c)(1),
(2) Date: Oct. 7, 2021

(87) PCT Pub. No.: WO2020/212297
PCT Pub. Date: Oct. 22, 2020

(65) Prior Publication Data

US 2022/0143107 A1 May 12, 2022

(30) Foreign Application Priority Data

Apr. 15, 2019 (EP) .................................... 19382287

(51) Int. Cl.
*A61K 35/741* (2015.01)
*A61K 9/48* (2006.01)

(52) U.S. Cl.
CPC .......... *A61K 35/741* (2013.01); *A61K 9/4808* (2013.01); *A61K 9/485* (2013.01); *A61K 9/4866* (2013.01)

(58) Field of Classification Search
None
See application file for complete search history.

(56) References Cited

U.S. PATENT DOCUMENTS

| | | | |
|---|---|---|---|
| 9,072,784 | B2 | 7/2015 | Rudolph et al. |
| 2004/0241772 | A1 | 12/2004 | Prato |
| 2005/0266069 | A1 † | 12/2005 | Simmons |
| 2007/0148149 | A1 | 6/2007 | Boettner et al. |
| 2012/0039998 | A1 | 2/2012 | Valla et al. |
| 2018/0078586 | A1 † | 3/2018 | Jones |
| 2020/0188310 | A1 † | 6/2020 | Yde |
| 2022/0143107 | A1 † | 5/2022 | Negre |

FOREIGN PATENT DOCUMENTS

| | | | |
|---|---|---|---|
| CN | 104095180 | A | 10/2014 |
| CN | 107206350 | A | 9/2017 |
| CN | 108567799 | A | 9/2018 |
| CN | 104922158 | B | 11/2018 |
| EP | 0636692 | A1 | 2/1995 |
| EP | 1699474 | † | 12/2009 |
| EP | 1699474 | B1 | 12/2009 |
| GB | 1190386 | A | 5/1970 |
| JP | 2004-538311 | A | 12/2004 |
| JP | 2007-508035 | A | 4/2007 |
| KR | 20080059605 | † | 6/2008 |
| KR | 20080059605 | A2 | 6/2008 |
| WO | 2004022031 | A2 | 3/2004 |
| WO | WO2004022031 | † | 3/2004 |
| WO | 2005/047489 | A1 | 5/2005 |
| WO | 2005063200 | A2 | 7/2005 |
| WO | WO2005063200 | † | 7/2008 |
| WO | 2009096908 | A2 | 8/2009 |

(Continued)

OTHER PUBLICATIONS

Awa, Kimie et al., "The Effect of Microcrystalline Cellulose.." AAPS PharmSciTech vol. 16, No. 4, 2015.
Awa et al. "The effect of microcrystalline cellulose crystallinity on the hydrophilic property of tablets and the hydrolysis of acetylsalicylic acid as active pharmaceutical ingredient inside tablets." AAPS PharmSciTech 16 (2015): 865-870.
Product Sheet for California Gold Nutrition, LactoBif Probiotics, 30 Billion CFU, 60 Veggie Capsules from https://iherb.com/pr/california-gold-nutrition-lactobif-probiotics-30-billion-cfu-60-veggie-capsules/64009, (available since May 20, 2015) 15 pp.
Product Sheet for Nature's Bounty, Acidophilus Probiotic, 120 Tablets from https://iherb.com/pr/nature-s-bounty-acidophilus-probiotic-120-tablets/32089?gclid=Cj0KCQiAg5meBhCyARIsAJrtdr7nssRIK7xpcYfCa4fLICsn4B2necLPSOwAeQZVyaa-2eMOA63EgtQaAncUEALw_wcB&gclsrc=aw.ds, (available since Mar. 14, 2011) 14 pp.

(Continued)

*Primary Examiner* — Tigabu Kassa
(74) *Attorney, Agent, or Firm* — Nixon Peabody LLP; Mark J. FitzGerald; Alissa R. Young

(57) ABSTRACT

The present invention provides a solid oral pharmaceutical composition comprising a pharmaceutically effective amount of living microorganisms and one or more pharmaceutically acceptable water absorbing excipient(s), wherein the composition has a water content, determined according to European Pharmacopoeia 9.4, section 2.5.12., from 0.5 to 30% with respect the total weight of the composition. The invention also provides processes for its preparation as well as it use in therapy. The live-cell based composition of the invention is stable at mild conditions.

11 Claims, No Drawings

(56) References Cited

FOREIGN PATENT DOCUMENTS

| | | | |
|---|---|---|---|
| WO | 2016178775 | A1 | 11/2016 |
| WO | 2018002331 | A1 | 1/2018 |
| WO | 2018140931 | A1 | 8/2018 |
| WO | 2019043051 | A1 | 3/2019 |
| WO | WO2019043051 | † | 3/2019 |

OTHER PUBLICATIONS

Shah et al. "Physico-mechanical characterization of the extrusion-spheronization process. Part II: Rheological determinants for successful extrusion and spheronization." Pharmaceutical research 12 (1995): 496-507.
Sonaglio et al. "Physical characterization of two types of microcrystalline cellulose and feasibility of microspheres by extrusion/spheronization." Drug development and industrial pharmacy 21.5 (1995): 537-547.
Sonaglio et al. "Factorial design in the feasibility of producing Microcel MC 101 pellets by extrusion/spheronization." International journal of pharmaceutics 115.1 (1995): 53-60.
Third-party Observation Against Application Number EP20716843.6A Publication No. 3955899, entitled "Long-Term Stable Live Fecal Microbiota Composition" issued Feb. 14, 2023.
Muley et al. "Extrusion-spheronization a promising pelletization technique: In-depth review." Asian journal of pharmaceutical sciences 11.6 (2016): 684-699.
"Water: semi-micro determination", 2018, European Pharmacopoeia 9.4, pp. 5107.
Hamilton et al. "Standardized frozen preparation for transplantation of fecal microbiota for recurrent Clostridium difficile infection." Am J Gastroenterol. 107(5):761-767 (2012).
Hecker et al. "Fecal microbiota transplantation by freeze-dried oral capsules of recurrent Clostridium difficile infection." Open Forum Infectious Diseases 3(2): ofw091 (2016).
Lee et al. "Frozen vs Fresh Fecal Microbiota Transplantation and Clinical Resolution of Diarrhea in Patients With Recurrent Clostridium difficile Infection: A Randomized Clinical Trial." JAMA 315(2): 142-149 (2016).
Satokari et al. "Simple faecal preparation and efficacy of frozen inoculum in faecal microbiota transplantation for recurrent Clostridium difficile infection—an observational cohort study." Aliment Pharmacol Ther. 41(I) :46-53 (2015).
Tian et al. "Freeze-dried, Capsulized Fecal Microbiota Transplantation for Relapsing Clostridium difficile Infection." J Clin Gastroenterol. 49(6): 537-538 (2015).
Youngster et al. "Oral, capsulized, frozen fecal microbiota transplantation for relapsing Clostridium difficile infection." JAMA 312(17): 1772-1778 (2014).
Awa, Kimie et al. The Effect of Microcrystalline Cellulose Crystallinity on the Hydrophilic Property of Tablets and the Hydrolysis of Acetylsalicylic Acid as Active Pharmaceutical Ingredient Inside Tablets AAPS PharmSciTech, vol. 16, No. 4, Aug. 2015.†

† cited by third party

LONG-TERM STABLE LIVE FECAL MICROBIOTA COMPOSITION

CROSS-REFERENCE TO RELATED APPLICATIONS

This application is a 35 U.S.C. § 371 National Phase Entry Application of International Application No. PCT/EP2020/060370 filed Apr. 14, 2020, which claims benefit under 35 U.S.C. § 119 (a) of EP application Ser. Nos. 19/382,287.1 filed Apr. 15, 2019, the contents of each of which are incorporated herein by reference in their entireties.

The present invention relates to stable live fecal microbiota containing composition.

BACKGROUND OF THE INVENTION

Fecal microbiota transplantation (FMT) is the transfer of fecal material containing microorganisms from a healthy individual into a diseased recipient.

Traditionally, transplantation to the upper gastrointestinal (GI) tract is achieved via naso-gastric, naso-duodenal, naso-jejunal intubation, or via esophagogastroduodenoscopy or push enteroscopy. Delivery to the lower GI tract is usually achieved by colonoscopy, sigmoidoscopy, or enema. All of these techniques suffer from shortcomings. For example, upper GI tract administration carries the risks of aspiration-related complications (particularly naso-gastric delivery) and is invasive and uncomfortable to recipients. Lower GI tract delivery techniques such as colonoscopy and sigmoidoscopy are also invasive and uncomfortable and are associated with significant costs and risks.

Accordingly, there remains a need for a safe, effective and less invasive manner for delivery of microbial communities to recipients (e.g., fecal matter transplant or fecal microbiota transplantation).

Two approaches have been pursued for developing encapsulated oral formulations of microbial communities: (a) flash-freezing of an aqueous stool solution, and (b) lyophilisation.

The first approach involves flash-freezing of an aqueous solution of stool in a glycerol and saline buffer. The aqueous solution preserves the viability of the microbial strains but produces capsules that are highly unstable as the aqueous character of the stool quickly degrades the water-soluble capsules. The physical instability of these capsules complicates mass-production and creates clinical hazards as the capsules can rupture during administration. Such instability requires that capsules have to be stored at −70/−80° C. until their use, moment wherein they have to be unfreezed. Such instability together with the need of "sophisticated" devices limit the application of fecal microbiota therapy (FMT) to the hospital environment, under special medical supervision. Thus, the subject to be treated has to go to the hospital, wherein there are all the appropriate means to freeze and unfreeze the capsules. This, however, can lead to a lack of treatment compliance, leading to patient unadherence.

Several attempts have been performed in order to reduce the aqueous component of the stool. Dewatering of the microbial community through techniques such as lyophilisation is one of the main routes. However, the dewatering process is physically demanding and reduces the viability of the microbes significantly. In addition, sometimes the dewatering of the microbial community is not enough to achieve the appropriate stability, and special containers have to be developed with that aim. As an example, KR20080059605 discloses the packaging of lyophilized bacteria in a container with a particular design to reduce the environment humidity in contact with the capsule. This Korean patent document provides, among others, stability data with the lyophilized bacteria with (Example 6) or without (Example 5) excipients. Example 6 provides data with capsules comprising lyophilized bacteria together with microcrystalline cellulose and magnesium stearate. It is remarkably that the capsule without excipients was more stable within the particular container than when the capsules were formulated with the excipients.

In spite of the efforts made until now, there is still the need of stable home-based FMT based on live bacterial cells.

SUMMARY OF THE INVENTION

The present inventors have developed live microbiota capsules stable enough to be stored at about 4° C. rather than at −65° C. or at −80° C., meaning that the capsules can be stored in a conventional freezer in the home of the recipient.

As it is shown below, the present inventors firstly prepared a mix of fecal microbiota pellet (obtained from an aqueous solution of the stool in glycerol) with microcrystalline cellulose (hereinafter also referred as "MCC") and a lubricant (magnesium stearate). When capsules were prepared with that mixture, it was found that they had a humidity content, following European Pharmacopoeia 9.4, section 2.5.12., of about 30% with respect the total weight of the composition (see Table 1 below).

Surprisingly, the inventors have found that said capsules, comprising live microbiota in an environment with a water content up to about 30%, were stable during 3 months at 4° C. (temperature which is equivalent to fridge temperature) even at such high humidity content. In this regard, Table 1 shows that the inclusion of the water absorbing excipient confers to the encapsulated live microbiota a stability which is of the same order as the one achieved with lyophilized microbiota. Therefore, the inclusion of the water absorbing excipient is an effective alternative to the lyophilisation technique (which is more "aggressive" with the bacteria viability).

This is something unpredictable in view of the prior art. As discussed above, the state of the art has taught two options to achieve stable encapsulated fecal microbiota: reducing the temperature to about −80° C., thus getting freezed fecal microbiota; or reducing as much as possible the water content by lyophilizing the fecal microbiota. Even recent publications have disclosed the encapsulation of lyophilized bacteria and the packaging of the resulting lyophilized bacteria in a special container which reduces even more the humidity content within the container (such as the Korean patent KR20080059605). Therefore, the invention provided herein, i.e. stable live fecal microbiota (which require a high humidity content when compared with lyophilization) at milder temperature is surprising in view of the state of the art.

The stability of the capsules was not only in terms of bacterial viability but also in terms of capsules' morphology. As provided below, no changes in terms of length, width or odor were found when the capsules formulated with the fecal microbiota and the water absorbing excipient (MCC) were stored at 4° C. for three months.

Altogether the composition of the invention, therefore, means a great advance in the field of FMT because the treatment can be done by the recipient at home, avoiding transportation to a medical clinic. In addition, it is advantageous because it can improve treatment compliance by offering an improved convenience to patients, therefore leading to an increased patient adherence.

Thus, in a first aspect the present invention provides a solid oral pharmaceutical composition comprising a pharmaceutically effective amount of living microorganisms and one or more pharmaceutically acceptable water absorbing excipient(s), wherein the mixture has a water content, determined according to European Pharmacopoeia 9.4, section 2.5.12., from 0.5 to 30% with respect the total weight of the composition.

In a second aspect the present invention provides a process for preparing an oral pharmaceutical composition as defined in the first aspect of the invention, the process comprising mixing living microorganisms with the one or more water absorbing excipient(s).

An advantage of the present invention compared to the prior art is that the process for obtaining the composition of the invention requires few steps under mild conditions (room temperature and humidity) which minimizes the risk of loss of viable bacteria.

In a third aspect, the present invention provides an oral pharmaceutical composition obtainable by the process as defined in the second aspect of the invention.

In a fourth aspect, the present invention provides the oral pharmaceutical composition as defined in the first or third aspect of the invention for use in therapy.

It is the first time that it is reported the ability of a water absorbing excipient in stabilizing encapsulated living microorganisms. In fact, from the data provided by the Korean patent KR20080059605, the skilled person would have expected that water absorbing excipients negatively affected the stability of the microbiota when the data provided in Examples 5 and 6 of the prior art were compared.

Without being bound to the theory, the present inventors believe that such surprising effect is due to the fact that the water absorbing excipient (such as MCC, as illustrated below) interacts with the water present in the fecal microbiota pellet, such as part of the water remains "free" and a minor amount is absorbed as "structured water", the latter giving rise to the formation of a molecular sponge. In this way, the solid pharmaceutical composition would comprise a content of water up to about 30% (which would correspond to the water content of the starting fecal microbiota pellet used in the preparation of the capsule), but a great part of that water would be within a kind of "sponge" (the physical formed taken by the absorbing excipient) formed. Such "sponge" could act as a water reservoir or protection barrier: the live microbiota within the capsule, under the particular environment conditions, could gradually use the water available in the capsule. Therefore, the water absorbing excipient is able to exert the stabilizing effect thanks to the water content in the mixture.

The above would explain why in the Korean patent 20080059605 the same water absorbing excipient (MCC) cannot provide such stabilizing effect: the excipient is not able to stabilize the microorganism because it cannot absorb enough water because (a) the bacteria are lyophilized (i.e., do not comprise a significant amount of water), and (b) the environment humidity content is low due to the particular design of the container.

Thus, in a fifth aspect, the present invention provides the use of a water absorbing excipient for stabilizing living microorganisms in a solid oral pharmaceutical composition.

Finally, the present invention further provides the solid oral composition as defined in the first or third aspect of the invention for use in the treatment of a disease associated with dysbiosis. This aspect can alternatively be formulated as the use of the solid oral composition as defined in the first or third aspect of the invention in the manufacture of a medicament for the treatment of a disease associated with dysbiosis. This aspect can alternatively be formulated as a method of treating or preventing a disease associated with dysbiosis, the method comprising administering a therapeutically effective amount of the composition as defined in the first or third aspect of the invention to a subject in need thereof.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition. In addition, for the purposes of the present invention, any ranges given include both the lower and the upper end-points of the range. Ranges given, such as temperatures, times, weights, and the like, should be considered approximate, unless specifically stated.

As provided above, in a first aspect the present invention refers to an oral solid pharmaceutical composition comprising living microorganisms and one or more water absorbing excipient(s).

The expression "therapeutically effective amount" as used herein, refers to the amount of living microorganisms that, when administered, is sufficient to prevent development of, or alleviate to some extent, one or more of the symptoms of the disease which is addressed. The particular dose of living microorganisms administered according to this invention will of course be determined by the particular circumstances surrounding the case, including the compound administered, the route of administration, the particular condition being treated, and the similar considerations.

The expression "pharmaceutical composition" refers to those compositions with a beneficial effect in humans and non-humans.

In one embodiment of the first aspect of the invention, optionally in combination with any of the embodiments provided below, the living microorganism is a probiotic microorganism or fecal microbiota. In another embodiment, optionally in combination with any of the embodiments provided above or below, the living microorganisms is fecal microbiota.

In the present context, the term "microbiota" refers to the community of microorganisms that occur (sustainably or transiently) in and on an animal subject, typically a mammal such as a human, including eukaryotes, archaea, bacteria, fungi such as yeasts, and viruses (including bacterial viruses i.e., phage). The fecal microbiota comprises an unknown but large number of types of microorganisms.

In another embodiment of the first aspect of the invention, optionally in combination with any of the embodiments provided above or below, the composition comprises one water absorbing excipient.

In another embodiment of the first aspect of the invention, optionally in combination with any of the embodiments provided above or below, the water absorbing excipient is selected from: a cellulose-based excipient or a pharmaceutically acceptable salt thereof; kaolinite; talc; palygorskite; sepiolite; colloidal silicon dioxide; and smectites (among which montmorillonite, saponite, and hectorite are the most widely used species). In another embodiment of the first aspect of the invention, optionally in combination with any of the embodiments provided above or below, the water absorbing excipient is a cellulose-based excipient. In another embodiment of the first aspect of the invention, optionally in combination with any of the embodiments provided above or below, the water absorbing excipient is a cellulose ether derivative (such as an alkyl (e.g. a $C_{1-10}$ alkyl) ether, hydroxyalkyl (e.g., HO—($C_{1-10}$)alkyl) ether, or carboxylakyl (e.g., OH(O)C—($C_{1-10}$)alkyl-ether, or a pharmaceutically acceptable salt thereof), a cellulose ester (such as cellulose acetate, cellulose triacetate, cellulose propionate, cellulose acetate propionate (CAP), cellulose acetate butyrate (CAB) derivative), or a mixture thereof (i.e., one or more ether derivative with one or more ether derivative, one or more ether derivative with one or more ester derivative, or one or more ester derivative with one or more ester derivative). In another embodiment of the first aspect of the invention, optionally in combination with any of the embodiments provided above or below, the cellulose-based excipient is selected from: methylcellulose, ethylcellulose, ethylmethylcellulose, hydroxyethylcellulose, hydroxyethylmethylcellulose. hydroxypropylcellulose, hydroxypropylmethylcellulose, hydroxypropylethylcellulose, carboxymethylcellulose, and microcrystalline cellulose (MCC). In one embodiment, optionally in combination with any of the embodiments provided above or below, the water absorbing excipient is an ether cellulose derivative. In another embodiment of the first aspect of the invention, optionally in combination with any of the embodiments provided above or below, the water absorbing excipient is MCC. In another embodiment of the composition of the first aspect of the invention, optionally in combination with any of the embodiments provided above, it comprises fecal microbiota and MCC.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutical acceptable salts are well known in the art. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutical acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, and ammonium. Representative alkali or alkaline earth metal salts include sodium, lithium, potassium, calcium, magnesium, and the like. Further pharmaceutical acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The pharmaceutical composition of the invention is characterized by a water content up to 30%. In one embodiment of the first aspect of the invention, optionally in combination with any of the embodiments provided above or below, the water content is from 1 to 30%, from 5 to 30% or from 9 to 30% with respect to the total weight of the composition. Alternatively, the pharmaceutical composition of the first aspect of the invention has a water content of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30% with respect the total weight of the composition.

In another embodiment of the first aspect of the invention, optionally in combination with any of the embodiments provided above or below, the solid oral pharmaceutical composition comprises a water content from 1 to 30%, from 5 to 30% or from 9 to 30% with respect to the total weight of the composition, and the water absorbing excipient is selected from: a cellulose-based excipient or a pharmaceutically acceptable salt thereof; kaolinite; talc; palygorskite; sepiolite; colloidal silicon dioxide; and smectites (among which montmorillonite, saponite, and hectorite are the most widely used species). In another embodiment of the first aspect of the invention, optionally in combination with any of the embodiments provided above or below, the solid oral pharmaceutical composition comprises a water content from 1 to 30%, from 5 to 30% or from 9 to 30% with respect to the total weight of the composition, and the water absorbing excipient is a cellulose-based excipient. In another embodiment of the first aspect of the invention, optionally in combination with any of the embodiments provided above or below, the solid oral pharmaceutical composition comprises a water content from 1 to 30%, from 5 to 30% or from 9 to 30% with respect to the total weight of the composition, and the water absorbing excipient is a cellulose ether derivative (such as an alkyl (e.g. a $C_{1-10}$ alkyl) ether, hydroxyalkyl (e.g., HO—($C_{1-10}$)alkyl) ether, or carboxylakyl (e.g., OH(O)C—($C_{1-10}$)alkyl-ether, or a pharmaceutically acceptable salt thereof), a cellulose ester (such as cellulose acetate, cellulose triacetate, cellulose propionate, cellulose acetate propionate (CAP), cellulose acetate butyrate (CAB) derivative), or a mixture thereof (i.e., one or more ether derivative with one or more ether derivative, one or more ether derivative with one or more ester derivative, or one or more ester derivative with one or more ester derivative). In another embodiment of the first aspect of the invention, optionally in combination with any of the embodiments provided above or below, the solid oral pharmaceutical composition comprises a water content from 1 to 30%, from 5 to 30% or from 9 to 30% with respect to the total weight of the composition, and the cellulose-based excipient is selected from: methylcellulose, ethylcellulose, ethylmethylcellulose, hydroxyethylcellulose, hydroxyethylmethylcellulose. hydroxypropylcellulose, hydroxypropylmethylcellulose, hydroxypropylethylcellulose, carboxymethylcellulose, and microcrystalline cellulose (MCC). In one embodiment, optionally in combination with any of the embodiments provided above or below, the solid oral pharmaceutical composition comprises a water content from 1 to 30%, from 5 to 30% or from 9 to 30% with respect to the total weight of the composition, and the water absorbing excipient is an ether cellulose derivative. In another embodiment of the first aspect of the invention, optionally in combination with any of the embodiments provided above or below, the water absorbing excipient is MCC. In another embodiment of the composition of the first aspect of the invention, optionally in combination with any of the embodiments provided above, the solid oral pharmaceutical composition comprises a water content from 1 to 30%, from 5 to 30% or from 9 to 30% with respect to the total weight of the composition, and further comprises fecal microbiota and MCC.

The water content is determined according to European Pharmacopoeia 9.4, section 2.5.12., "water: semi-micro determination", page 5107, which is based on the reaction of water with sulfur dioxide and iodine in a suitable anhydrous medium in the presence of a base with sufficient buffering capacity. The measure is made with an apparatus consisting of a titration vessel with two identical platinum electrodes.

In another embodiment of the first aspect of the invention, optionally in combination with any of the embodiments provided above or below, the composition comprises one or more additional pharmaceutically or veterinary acceptable excipients.

The expression "pharmaceutically or veterinary acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio. Examples of suitable pharmaceutically acceptable excipients are lubricants, cryoprotectants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In one embodiment of the composition of the first aspect of the invention, optionally in combination with any of the embodiments provided above or below, it further comprises one or more pharmaceutically acceptable excipient(s) selected from: a cryoprotectant, a lubricant, and a combination thereof.

The composition may comprise at least one cryoprotectant. Examples of cryo-protectants which can be used are glycerol, carbohydrate, water soluble antioxidants such as sodium ascorbate, glutathione, riboflavin, L-cysteine, and pharmaceutically acceptable salts or combinations thereof. In one embodiment of the composition of the first aspect of the invention, optionally in combination with any of the embodiments provided above or below, the composition comprises a cryoprotectant. In another embodiment of the composition of the first aspect of the invention, optionally in combination with any of the embodiments provided above or below, the composition comprises glycerol.

In another embodiment of the composition of the first aspect of the invention, optionally in combination with any of the embodiments provided above or below, it comprises a cryoprotectant and a lubricant. In another embodiment of the first aspect of the invention, optionally in combination with any of the embodiments provided above or below, the composition further comprises glycerol and a lubricant. In another embodiment of the first aspect of the invention, optionally in combination with any of the embodiments provided above or below, the composition further comprises a cryoprotectant and a stearate salt. In another embodiment of the first aspect of the invention, optionally in combination with any of the embodiments provided above or below, the composition further comprises glycerol and a stearate salt. In another embodiment of the first aspect of the invention, optionally in combination with any of the embodiments provided above or below, the composition further comprises glycerol and magnesium stearate.

In another embodiment of the first aspect of the invention, optionally in combination with any of the embodiments provided above or below, the composition comprises: fecal microbiota, a cellulose derivative, a stearate salt, and a cryoprotectant. In another embodiment of the first aspect of the invention, optionally in combination with any of the embodiments provided above or below, the composition comprises: fecal microbiota, a cellulose ether derivative, a stearate salt, and glycerol. In another embodiment of the first aspect of the invention, optionally in combination with any of the embodiments provided above or below, the composition comprises: fecal microbiota, MCC, a stearate salt, and glycerol. In another embodiment of the first aspect of the invention, optionally in combination with any of the embodiments provided above or below, the composition comprises: fecal microbiota, MCC, a stearate salt, and glycerol. In another embodiment of the first aspect of the invention, optionally in combination with any of the embodiments provided above or below, the composition comprises: fecal microbiota, a cellulose ether derivative, magnesium stearate, and glycerol. In another embodiment of the first aspect of the invention, optionally in combination with any of the embodiments provided above or below, the composition comprises: fecal microbiota, MCC, magnesium stearate, and glycerol.

In another embodiment of the first aspect of the invention, optionally in combination with any of the embodiments provided above or below, the oral solid pharmaceutical composition is a capsule, i.e., a single capsule, such as a hard capsule or a soft capsule. In the present invention the expression "single capsule" means that the oral pharmaceutical composition consists of only one capsule comprising the microbiota and the adsorbant(s). Therefore, this embodiment (i.e., the "single capsule") does not encompass the possibility that the capsule comprising the microbiota and the adsorbant(s) is within another capsule. In another embodiment of the first aspect of the invention, optionally in combination with any of the embodiments provided above or below, the solid oral pharmaceutical composition consists of a single capsule made of the microbiota and the adsorbant(s).

As used herein the term "capsule" refers to a conventional hard capsule intended for oral administration to a human or animal being. The capsules of the present invention do not structurally depart from the conventional definition of hard capsules. When reference is made herein to "capsule" it refers to the outer or inner capsule or the outer capsule comprising the inner capsule unless the context indicates otherwise. Generally, the term "capsule" refers to both empty and filled capsules whereas "shell" specifically refers to an empty capsule.

As known to the person of ordinary skill in the art, commercially available capsules provided as ordinary capsules or elongated capsules are named by numbers and the suffix el for elongated capsules.

A further advantage is that the production of the capsules of the invention does not require drying which can lead to a significant loss of viable bacteria: just filling the mixture in the capsule (by any of the routine techniques to the skilled in the art).

In one embodiment of the first aspect of the invention, optionally in combination with any of the embodiments provided above or below, the composition is an enteric capsule. The term "enteric capsules" means such capsules having enteric properties. "Enteric properties" means that the capsule can be soluble in or disintegrated by the alkaline intestinal secretions but being substantially insoluble or resistant to solution in the acid secretions of the stomach. There are also commercially available enteric capsules to fill with the mixture provided by the invention.

All the embodiments provided under the first aspect of the invention are also embodiments of the second, third, fourth and fifth aspects.

The present invention provides in a second aspect a process for preparing the composition of the first aspect of the invention.

In one embodiment, the process is performed at temperature and relative humidity room conditions.

The term "room temperature" refers to a temperature, without heating or cooling, from 15 to 25° C.

The term "relative humidity room conditions" means that the process is performed at the relative humidity of the air. In one embodiment optionally in combination with any of the embodiments provided above or below, the relative humidity is from 50 to 80%. In one embodiment optionally in combination with any of the embodiments provided above or below, the relative humidity is 60%±5%.

In one embodiment of the second aspect of the invention, optionally in combination with any of the embodiments provided above or below, the process comprises mixing an excess by weight of the excipient(s) with respect to the amount of living microorganism, which is expressed in volume units. When the composition of the invention comprises more than one water absorbing excipient, the expression "excess by weight of the excipients" means that the total amount of water absorbing excipients is in excess with respect to the volume of living microorganism.

In another embodiment of the second aspect of the invention, optionally in combination with any of the embodiments provided above or below, the ratio between the amount of living microorganisms expressed in volume units and the amount of water absorbing excipient(s), expressed in weight units, is comprised from 0.1:1 to 0.99:1, preferably from 0.70:1 to 0.95:1. When the composition of the invention comprises more than one water absorbing excipient, the expression "amount of water absorbing excipients" refers to the total amount of these excipients.

In another embodiment of the second aspect of the invention, optionally in combination with any of the embodiments provided above or below, the composition comprises a lubricant and the weight ratio between the water absorbing agent(s) and the lubricant is comprised from 30:1 to 70:1, preferably from 40:1 to 60:1, more preferably 50:1.

In another embodiment of the second aspect of the invention, optionally in combination with any of the embodiments provided above or below, the living microorganism is a fecal microbiota extract.

The fecal microbiota extract can be prepared by a process comprising the steps of: (a) providing a fecal material obtained from a suitable donor; and (b) subjecting the fecal material to at least one processing step under conditions such that a homogenized composition of bacteria, archaea, fungi, and viral, is produced from the fecal material.

The fecal material should be protected from oxygen e.g. by covering the sample immediately after producing it with oxygen reduced saline solution and by doing most of the processing in an anaerobic environment either by using an anaerobic chamber or by flushing with e.g. Ar, $N_2$ or $CO_2$.

In one embodiment of the second aspect of the invention, optionally in combination with any of the embodiments provided above or below, feces and saline are homogenized, filtered and centrifuged. The supernatant is discarded, and the pellet mixed with glycerol as a cryo-protectant to provide fecal microbiota extract.

In another embodiment of the second aspect of the invention, optionally in combination with any of the embodiments provided above or below, the process comprises:

(a) obtaining a fecal microbiota extract;

(b) mixing the fecal microbiota extract with one or more water absorbing excipients as defined in any of the embodiments provided above.

In another embodiment of the second aspect of the invention, optionally in combination with any of the embodiments provided above or below, the process comprises:

(a) obtaining a fecal microbiota extract by: (a.1) homogenising feces with saline, (a.2) filtering the solution, (a.3) centrifugation, and (a.4) mixing the pellet with a cryoprotectant;

(b) mixing the fecal microbiota extract with one or more water absorbing excipients as defined in any of the embodiments provided above.

In another embodiment of the second aspect of the invention, optionally in combination with any of the embodiments provided above or below, the process comprises:

(a) obtaining a fecal microbiota extract by: (a.1) homogenising feces with saline, (a.2) filtering the solution, (a.3) adding a cryoprotectant, and (a.4.) centrifugation;

(b) mixing the fecal microbiota extract with one or more water absorbing excipients as defined in any of the embodiments provided above.

In another embodiment of the second aspect of the invention, optionally in combination with any of the embodiments provided above or below, the process comprises:

(a) obtaining a fecal microbiota extract by: (a.1) homogenising feces with saline and a cryoprotectant (such as glycerol), wherein the % in volume of cryoprotectant vs the total volume of solution is from 5-15% or 5, 6, 7, 8, 9, 10, 11, 12, 13, 14 or 15% (v/v), (a.2) filtering the solution, (a.3) adding a cryoprotectant at a % in volume vs the total volume of solution from 10 to 50%, from 10 to 40%, from 15 to 35% or 15, 16, 17, 18, 19, 20, 21, 22, 23, 24, 25, 26, 27, 28, 29, 30, 31, 32, 33, 34 or 35% (v/v), and (a.4) centrifuging; and (b) mixing the fecal microbiota extract with one or more water absorbing excipients as defined in any of the embodiments provided above.

In another embodiment of the second aspect of the invention, optionally in combination with any of the embodiments provided above or below, the process comprises:

(a) obtaining a fecal microbiota extract by: (a.1) homogenising feces with saline and a cryoprotectant (such as glycerol), wherein the % in volume of cryoprotectant vs the total volume of solution is 10% (v/v), (a.2) filtering the solution, (a.3) adding a cryoprotectant at a % in volume vs the total volume of solution of 20% (v/v), and (a.4) centrifuging; and (b) mixing the fecal microbiota extract with one or more water absorbing excipients as defined in any of the embodiments provided above.

In another embodiment of the second aspect of the invention, optionally in combination with any of the embodiments provided above or below, the process comprises:

(a) obtaining a fecal microbiota extract by: (a.1) homogenising feces with saline, (a.2) filtering the solution, (a.3) centrifugation, and (a.4) mixing the pellet with a glycerol;
(b) mixing the fecal microbiota extract with one water absorbing excipient as defined in any of the embodiments provided above.

In another embodiment of the second aspect of the invention, optionally in combination with any of the embodiments provided above or below, the process is performed to obtain a capsule and it comprises:

(a) obtaining a fecal microbiota extract;
(b) mixing the fecal microbiota extract with one or more water absorbing excipients as defined in any of the embodiments provided above;
(c) adding one or more further pharmaceutically acceptable excipients; and
(d) encapsulating the resulting mixture.

In another embodiment of the second aspect of the invention, optionally in combination with any of the embodiments provided above or below, the process is performed to obtain a capsule and it comprises:

(a) obtaining a fecal microbiota extract by: (a.1) homogenising feces with saline, (a.2) filtering the solution, (a.3) centrifugation, and (a.4) mixing the pellet with a cryoprotectant;
(b) mixing the fecal microbiota extract with one water absorbing excipients as defined in any of the embodiments provided above;
(c) adding one or more pharmaceutically acceptable excipients; and
(d) encapsulating the resulting mixture.

In another embodiment of the second aspect of the invention, optionally in combination with any of the embodiments provided above or below, the process is performed to obtain a capsule and it comprises:

(a) obtaining a fecal microbiota extract by: (a.1) homogenising feces with saline, (a.2) filtering the solution, (a.3) centrifugation, and (a.4) mixing the pellet with a cryoprotectant;
(b) mixing the fecal microbiota extract with one or more water absorbing excipients as defined in any of the embodiments provided above;
(c) adding a lubricant; and
(d) encapsulating the resulting mixture.

In another embodiment of the second aspect of the invention, optionally in combination with any of the embodiments provided above or below, the process is performed to obtain a capsule and it comprises:

(a) obtaining a fecal microbiota extract by: (a.1) homogenising feces with saline, (a.2) filtering the solution, (a.3) centrifugation, and (a.4) mixing the pellet with a cryoprotectant;
(b) mixing the fecal microbiota extract with a cellulose-based excipient as defined in any of the embodiments provided above;
(c) adding one or more further pharmaceutically or veterinary acceptable excipients; and
(d) encapsulating the resulting mixture.

In another embodiment of the second aspect of the invention, optionally in combination with any of the embodiments provided above or below, the process is performed to obtain a capsule and it comprises:

(a) obtaining a fecal microbiota extract by: (a.1) homogenising feces with saline, (a.2) filtering the solution, (a.3) centrifugation, and (a.4) mixing the pellet with a cryoprotectant;
(b) mixing the fecal microbiota extract with a cellulose derivative as defined above;
(c) adding a lubricant; and
(d) encapsulating the resulting mixture.

In another embodiment of the second aspect of the invention, optionally in combination with any of the embodiments provided above or below, the process is performed to obtain a capsule and it comprises:

(a) obtaining a fecal microbiota extract by: (a.1) homogenising feces with saline, (a.2) filtering the solution, (a.3) centrifugation, and (a.4) mixing the pellet with a cryoprotectant;
(b) mixing the fecal microbiota extract with MCC;
(c) adding a stearate salt; and
(d) encapsulating the resulting mixture.

In another embodiment of the second aspect of the invention, optionally in combination with any of the embodiments provided above or below, the process is performed to obtain a capsule and it comprises:

(a) obtaining a fecal microbiota extract by: (a.1) homogenising feces with saline, (a.2) filtering the solution, (a.3) centrifugation, and (a.4) mixing the pellet with a cryoprotectant;
(b) mixing the fecal microbiota extract with MCC, wherein the amount of MCC, expressed in weight units, is added in excess with respect to the amount of fecal microbiota extract, expressed in volume units;
(c) adding a stearate salt; and
(d) encapsulating the resulting mixture.

In another embodiment of the second aspect of the invention, optionally in combination with any of the embodiments provided above or below, the process is performed to obtain a capsule and it comprises:

(a) obtaining a fecal microbiota extract by: (a.1) homogenising feces with saline, (a.2) filtering the solution, (a.3) adding a cryoprotectant, (a.4.) centrifugation, and (a.5.) extraction;
(b) mixing the fecal microbiota extract with one or more water absorbing excipients as defined in any of the embodiments provided above;
(c) adding one or more further pharmaceutically acceptable excipients, such as a lubricant; and
(d) encapsulating the resulting mixture.

In another embodiment of the second aspect of the invention, optionally in combination with any of the embodiments provided above or below, the process is performed to obtain a capsule and it comprises:

(a) obtaining a fecal microbiota extract by: (a.1) homogenising feces with saline and a cryoprotectant (such as glycerol), wherein the % in volume of cryoprotectant vs the total volume of solution is from 5-15% or 5, 6, 7, 8, 9, 10, 11, 12, 13, 14 or 15% (v/v), (a.2) filtering the solution, (a.3) adding a cryoprotectant at a % in volume vs the total volume of solution from 10 to 50%, from 10 to 40%, from 15 to 35% or 15, 16, 17, 18, 19, 20, 21, 22, 23, 24, 25, 26, 27, 28, 29, 30, 31, 32, 33, 34 or 35% (v/v), (a.4) centrifuging, and (a.5.) isolation of the extract;

(b) mixing the fecal microbiota extract with one or more water absorbing excipients as defined in any of the embodiments provided above;

(c) adding one or more further pharmaceutically acceptable excipients, such as a lubricant; and (d) encapsulating the resulting mixture.

In another embodiment of the second aspect of the invention, optionally in combination with any of the embodiments provided above or below, the process is performed to obtain a capsule and it comprises:

(a) obtaining a fecal microbiota extract by: (a.1) homogenising feces with saline and a cryoprotectant (such as glycerol), wherein the % in volume of cryoprotectant vs the total volume of solution is 10% (v/v), (a.2) filtering the solution, (a.3) adding a cryoprotectant at a % in volume vs the total volume of solution of 20% (v/v), and (a.4) centrifuging, and (a.5.) isolation of the extract;

(b) mixing the fecal microbiota extract with one or more water absorbing excipients as defined in any of the embodiments provided above;

(c) adding one or more further pharmaceutically acceptable excipients, such as a lubricant; and (d) encapsulating the resulting mixture.

The solid composition of the invention is useful for populating the gastrointestinal tract of any subject such as a human recipient by oral administration to the subject of an effective amount of a composition comprising microorganisms. Depending on the severity and present status of the disease, disorder or condition the recipient may be considered a patient and the term "subject in need thereof" includes both. Unless the context indicates otherwise, all three terms are meant to designate the human or animal ingesting one or more of the capsules of the invention.

The term "subject" as used herein refers to any mammal, including, but not limited to, livestock and other farm animals (such as cattle, goats, sheep, horses, pigs and chickens), performance animals (such as racehorses), companion animals (such as cats and dogs), laboratory test animals and humans. Typically, the subject is a human.

The capsules comprising the composition may treat, prevent, delay or reduce the symptoms of diseases associated with a dysbiosis (microbial imbalance or maladaptation on or inside the body). More specifically, the capsules of the present invention may be useful for preventing or treating an infection caused by *C. difficile*, *Salmonella* spp., enteropathogenic *E. coli*, multi-drug resistant bacteria such as *Klebsiella*, and *E. coli*, Carbapenem-resistent Enterobacteriaceae (CRE), extended spectrum beta-lactam resistant Enterococci (ESBL), and vancomycin-resistant Enterococci (VRE).

In some embodiments, the subject has inflammatory bowel diseases (IBD), for example, Crohn's disease, colitis (e.g., ulcerative colitis or microscopic colitis), or pouchitis; or has irritable bowel syndrome or functional dyspepsia. In some embodiments, the subject has hepatic disease, such as non-alcoholic steatohepatitis (NASH), non-alcoholic fatty liver disease (NAFLD), hepatic encephalopathy, primary sclerosing cholangitis (PSC), autoimmune hepatitis, or drug-induced liver injury. In some embodiments, the subject has an autoimmune disease such as celiac disease or eosinophilic esophagitis. In some embodiments, the subject has a hyperproliferative disease or malignancy of the GI, such as colorectal cancer/polyps, esophageal cancer or Barett's esophagus. In some embodiments, the subject has metabolic disease, such as metabolic syndrome, Type 1 or Type 2 diabetes, obesity, malnutrition or undernutrition, or cardiovascular disease (e.g., atherosclerosis). In other embodiments, the subject has rheumatologic disease, such as inflammatory arthritis (rheumatoid arthritis or RA, ankylosing spondylitis, psoriatic arthritis, IBD spondyloarthropathy), fibromyalgia, chronic fatigue syndrome, or an autoimmune and connective tissue disorder (e.g., systemic lupus erythematosus, scleroderma, and Sjogren's syndrome). In some embodiments, the subject has vasculitis (e.g., polymyalgia rheumatic/giant cell arteritis or polyarteritis nodosa). In some embodiments, the subject has a psychiatric disorder such as mood disorder (e.g., depression or bipolar disorder), anxiety disorder (e.g., general anxiety disorder, post-traumatic stress disorder), or developmental disorder (e.g., autism spectrum disorder, attention deficit hyperactivity disorder). In some embodiments, the subject has one or more of colonic polyps, cysts, diverticular disease, constipation, intestinal obstruction, malabsorption syndrome, ulceration of the mucosa, and diarrhea. Other examples of diseases or disorders which may be treated with the capsule of the invention are atopic dermatitis, rhinitis and upper respiratory tract infection (URTI).

As the microbiome of subjects with chronic disease or disorder tends to revert back to one's own intrinsic abnormal microbiome, repeated administration of microbial communities may be needed to ensure a sustained clinical cure. Accordingly, the composition of the invention comprising microorganisms may be delivered as maintenance doses. The maintenance dosing regimen may vary, including by microbial dose, frequency of administration, administration interval and length, and depending on the disease and biology of the subject.

For example, therapy of chronic medical disease may require a dose of about 5 to about 50 capsules for induction therapy, such as about 5 to about 40 capsules per administration. For example, the composition may be administered at a dose of about 10, about 15, about 20, about 25, about 30, about 35, about 40, about 45, or about 50 capsules per administration. A subject may be treated one or more times. For maintenance therapy, capsules may be administered daily, or from two to five times weekly, or from one to ten times monthly. Maintenance therapy may proceed for several weeks to several months. For example, maintenance therapy may proceed for about two to about six weeks (e.g., about one month), or may proceed for about two to about six months (e.g., from about two to four months) or even longer. An "administration" refers to the capsules ingested over the course of a single day.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1

A pool of fresh refrigerated faeces (300 g) was transferred to stomacher bags in which 0.9% NaCl 1:10 were added. It was introduced into Stomacher 400 circulator (Seward Ltd., Sussex, United Kingdom) for 1 minute at 230 rpm obtaining a slurry. The mix was transferred into labelled plastic tubes with 50 ml of capacity and 10% pure Glycerol (99%) was added before freezing at −80° C.

To continue processing, samples were unfrozen overnight at 4° C. and 20% glycerol (99%) was added. Then the mix was centrifuged at 400 G for 20 minutes at 4° C. (Heraeus Megafuge 16R Centrifuge, Thermo Fisher Scientific Inc., MA, USA) to remove sample debris. The supernatant was transferred into high resistant tubes previously filtered with conventional sieve to eliminate possible detritus and the volume was centrifuged at 10000 g for 30 minutes at 4° C. (Sorvall Evolution RC Centrifuge, Thermo Fisher Scientific Inc., MA, USA) to obtain a microbial pellet. The supernatant was eliminated by decantation and the pellet was recovered with a spatula avoiding any remaining supernanant.

The pellet was separated into 2 parts for lyophilisation (comparative purpose) and adsorption experiments (invention), each one with 3 identical aliquots to do the experiments per triplicate containing an equivalent of 50 g faeces each one.

A. Preparation of a Capsule According to the Invention 9.3 mL aliquots were mixed with 10 g of microcrystalline cellulose (Vivapur®-101), thus obtaining an adsorbate. The generation of the adsorbate can be appreciated because the aliquot changes its appearance from a liquid texture to a “sawdust-type” texture. With the aim of helping in the encapsulation, 200 mg of magnesium stearate were further added to the adsorbate.

Once obtained the adsorbate and before encapsulating, the product was kept overnight at 4° C. in a fridge. The product was surrounded of silica gel plaques to reduce/eliminate the fridge’s humidity surrounding the mixture.

Finally, the adsorbate thus obtained was encapsulated with semi-automated encapsulator FagronLAB™ FG (Fagron Iberica, Barcelona, Spain) into acid-resistant capsule size n°00.

B. Preparation of a Capsule with Lyophilized Microbiota (Comparative Purposes)

The lyophilisation procedure was performed using Telstar LIOLAB 3 and following manufacturer’s instructions.

The lyophilizates thus obtained were encapsulated with semi-automated encapsulator FagronLAB™ FG (Fagron Iberica, Barcelona, Spain) into acid-resistant capsule size n°00.

C. Bacterial Viability Analysis

Bacterial amounts and viability from the initial pool, pellet and capsules from each replicate at time 0, 1 and 3 months after keeping samples at 4° C. using LIVE/DEAD™ Baclight™ Bacterial Viability and Counting Kit (Thermo Fisher Scientific, MA, USA) for flow cytometry and quantitative bacterial culture in Columbia Agar with 5% sheep blood (Becton Dickinson GmbH, Germany). The cytometer used was BD FACSCantoll (BD Biosciences, CA, USA) and software was BD FACSDiva 8.0 following manufacturer’s instructions. The ratio Syto9:propidium iodide at was optimized to 1:1 using 0.1 μl in a final volume of 250 μl of sample. The optimum dilution of the sample to be analysed was found to be 1:10000.

For the flow cytometry analysis, testing aliquots of capsules and non-encapsulated adsorbate and lyophilized were diluted at 1:10000 as explained above with a 0.9% NaCl solution and vortexed vigorously until obtaining homogeneous liquid. A dilution in 0.9% NaCl was performed to achieve a bacterial dilution of $10^{-4}$ (1:10000) in which SYTO9 and Propidium Iodide at a 1:1 proportion (0.1 μl of Syto9 and 0.1 μl of Propidium Iodide at a final volume of 250 microliters), and 10 μl of microspheres (1/2-diluted) included in the kit. Once obtained the results, the concentration of live bacteria was determined following the equation of the protocol:

$$\frac{((\text{events in } \textit{bac.} \text{ region}\} \times (\text{dilution factors}\})}{((\text{events in bead region}) \times (\text{dilution of beads}))} = \text{bacteria/mL}$$

D. Stability and Morphological Analysis

Possible morphological changes as well as the humidity of lyophilized and capsules of the invention both from the mixture prepared as explained above, and kept under 4° C. with or without silica gel, using Karl-Fischer method (Metrohm 899 coulometer), according to Pharmacopoeia 9.4., section 2.5.12. The humidity was tested in 3 capsules individually for each condition using Hydranal-Coulomat AG as a reactive. From the content of each capsule, 100 mg was taken as aliquot and was analysed with agitation parameter rate=10.

Results

From each aliquot representing 50 g of faeces 3 capsules of lyophilized were obtain, whereas in adsorbate capsules, between 14 and 17 capsules were obtained. No morphological changes (in terms of length or width of the capsule) nor smells in any of the capsules were identified during the 3 months of the study.

TABLE 1

Results from bacterial culture and flow cytometry analysis of capsules. The results show the viability (i.e., the amount of live microbiota)

| | Time 0 n/a | | 3 months 4° C. | |
|---|---|---|---|---|
| Sample | Bacterial culture | Flow cytometry | Bacterial culture | Flow cytometry |
| Pool (CFU/ml) | 3.32E+07 | 9.10E+08 | | |
| Pellet (CFU/ml) | 1.50E+08 | 1.53E+10 | | |
| Lyophilized capsule (CFU/capsule) | 3.98E+09 | 1.12E+11 | 6.41E+09 | 1.34E+11 |
| Capsule of the invention (CFU/capsule) | 1.61E+09 | 1.12E+10 | 1.23E+09 | 1.44E+10 |

As one can see, the capsules of the invention were stable after three months at 4° C. When a characterization of the water content was performed, it was found that the capsules of the invention comprised a very high water content (see Table 2 below). So high content should negatively affect the viability of the cells (in fact, the skilled person would expect a remarkably exponential cell growth).

Contrary to that, the bacterial population was substantially maintained as at the beginning of the test thanks to the inclusion of the water absorbing excipient.

The inventors have repeated the same steps but omitting the addition of magnesium stearate. It is also concluded that the same “protective effect” is providing by the water absorbing excipient to the microbiota.

TABLE 2

Results of humidity in the capsules of the invention

| Determination | Method | Condition | Sample | Result | Media | Sn-1 | CV (%) |
|---|---|---|---|---|---|---|---|
| % $H_2O$ | Ph. Eur 9.6 (2.5.12) | Direct encapsulation | 1 | 28.95% | 27.83% | 0.98 | 3.54% |
| | | | 2 | 27.46% | | | |
| | | | 3 | 27.09% | | | |
| | | Encapsulation after dessecation with Silica Gel | 1 | 10.33% | 9.76% | 0.68 | 7.00% |
| | | | 2 | 9.95% | | | |
| | | | 3 | 9.00% | | | |

Example 2

Material/Methods

In order to analyse alive bacterial concentration and microbial composition over time up to 6 months at 4° C., 2 samples from 50 g of faeces (named M1, and M2) from 2 different volunteers were obtained.

Each sample was processed separately following the previous described protocol and adsorbate capsules were obtained:

(a) by adding only Vivapur-101 (i.e. microcrystalline cellulose) as adsorbent (samples M1V and M2V); and (b) by adding Vivapur-101 in combination to magnesium stearate, as disclosed above (samples M1VS and M2VS).

The ratio between the volume of the aliquote (expressed in “mL”) and the amount of adsorbant and magnesium stearate (expressed in “g”) was substantially the same as pointed out in Example 1 above.

Bacterial concentration by flow cytometry and genomic analysis by 16S sequencing were tested from original samples, after processing and centrifugations (pellet) and once obtained the adsorbate with the two combinations of excipients (M1V, M2V, M1VS, and M2VS).

For Flow cytometry, the LIVE/DEAD BACLIGHT STAINING AND COUNTING KIT (ThermoFisher) was used, and for genomic analysis DNA was extracted using PureLink™ Microbiome DNA Purification kit (Invitrogen) and regions V3-V4 from 16S rRNA gen were sequenced with Miseq platform (Illumina) using KAPA HiFi HotSart polymerase (Roche). With the sequencing data obtained, the taxonomical composition was determined and the alpha diversity of the samples was also calculated in order to check product stability in terms of microbial composition.

Alpha diversity refers to the species richness and diversity in each sample. For this determination, Faith diversity Index or Phylogenetic diversity (PD) which is calculated as the number of different species detected in a sample including the phylogenetic distance between them in a clandogram using qiime2 platform (www.qiime2). The diversity analysis was useful to observe if there was a loss of bacterial diversity during the production and storage of the product.

Statistical analysis was performed with Paired t-test considering $p<0.05$ to be statistically significant, in order to test the difference between the results using R 3.6.2. version and graphs were obtained with GraphPad Prism 8.02.

Results

Bacterial Concentration Analysis

TABLE 3

Results from flow cytometry.

| Alive bacteria/50 g faeces | M1V | M2V |
|---|---|---|
| Capsules t = 0 | 2.02E+11 | 1.28E+11 |
| Capsules t = 6 months | 1.05E+11 | 1.21E+11 |

The results showed that in MV group there were no significant differences between capsules at t=0 (p=0.125) and t=6 (p=0.029).

These results corroborate that the main responsible of providing a surprising stabilizing effect on bacterial viability up to 6 months at 4° C. is the adsorbant mixed with the fecal microbiota.

Genomic Analysis

Once it was confirmed that the capsules of the invention comprised a high number of viable cells, maintained over time, the next step was to confirm whether the original bacterial diversity from the donor sample was also maintained. This is also relevant because the longer the bacterial diversity is maintained, the greater the efficacy can be.

TABLE 4

Results from alpha diversity using Faith Index (PD).

| Alpha diversity (faith index) | M1V | M1VS | M2VS |
|---|---|---|---|
| Original | 9.641666008 | 9.641666008 | 8.38365486 |
| Capsules t = 6 months | 9.570578536 | 9.951546215 | 8.47101626 |

From these results, it could be concluded that there were no significant differences between original sample and capsule at 6 months (p=0.922) when the capsule was formulated with the adsorbant (MV1). Which means that the inclusion of the adsorbant provides an appropriate environment which respects and substantially maintains the full diversity of the original microbiota.

Table 4 also shows that the inclusion of a further excipient in the capsule according to the invention, did not change the behaviour provided by the adsorbant and no significant differences were detected between the original samples and the capsules at 6 months (M1VS and M2VS). This is indicative of the strong beneficial stabilizing effect provided by the adsorbant because, even incorporating other excipients for the optimized manufacture of the capsules, such stabilizing effect is not negatively affected, being substantially retained the original diversity of the starting microbiota sample.

CITATION LIST

Patent Literature

KR20080059605.

Non Patent Literature

Section 2.5.12: Water: semi-micro determination, "European Pharmacopoeia 9.4", 2018, page 5107

What is claimed is:

1. A method for treating dysbiosis in a subject in need thereof, the method comprising: administering a solid oral pharmaceutical composition to a subject in need thereof, wherein the solid oral pharmaceutical composition comprises a pharmaceutically effective amount of non-lyophilized living fecal microbiota extract in admixture with one or more pharmaceutically acceptable water absorbing excipients comprising microcrystalline cellulose (MCC), wherein the ratio between the amount of living microorganisms expressed in volume units and the amount of water absorbing excipient(s), expressed in weight units, is from 0.1:1 to 0.99:1, wherein the composition has a water content, determined according to European Pharmacopoeia 9.4, section 2.5.12, from 0.5% to 30% with respect to the total weight of the composition, wherein alpha diversity of the non-lyophilized living microorganisms in the solid oral pharmaceutical composition is not significantly different than the alpha diversity of the non-lyophilized living microorganisms before admixture with the one or more water-absorbing excipients, and wherein the solid oral pharmaceutical composition is stable at 4° C. for 3 months.

2. The method of claim 1, wherein the solid oral pharmaceutical composition further comprises one or more additional pharmaceutically acceptable excipients.

3. The method of claim 1, wherein the solid oral pharmaceutical composition further comprises one or more of a cryoprotectant, a lubricant, a stearate salt, and glycerol.

4. The method of claim 1, wherein the alpha diversity of the non-lyophilized living microorganisms is substantially maintained for at least 6 months of storage at 4° C.

5. The method of claim 1, wherein alpha diversity comprises Faith Diversity Index.

6. The method of claim 1, wherein the subject has irritable bowel syndrome (IBS).

7. The method of claim 1, wherein the subject has hepatic encephalopathy.

8. The method of claim 1, wherein the solid oral pharmaceutical composition is a single capsule.

9. The method of claim 2, wherein the one or more additional water absorbing excipients is selected from: a cellulose-based excipient or a pharmaceutically acceptable salt thereof; kaolinite; talc; palygorskite; sepiolite; and smectites.

10. The method of claim 2, wherein the one or more additional water absorbing excipients is a cellulose ether derivative, a cellulose ester derivative, or a combination thereof.

11. The method of claim 1, wherein the solid oral pharmaceutical composition further comprises a lubricant, the weight ratio of water absorbing agent(s):lubricant being comprised from 30:1 to 70:1.

* * * * *